United States Patent
O'Connell, Sr. et al.

(10) Patent No.: US 10,064,758 B2
(45) Date of Patent: Sep. 4, 2018

(54) METHOD, APPARATUS AND COMPUTER PROGRAM FOR PROVISION OF METEROLOGICAL DATA TO ASSIST IN TIMING OF REMEDY TO AMELIORATE PHYSICAL DISTRESS

(71) Applicant: CIRRUS HEALTHCARE PRODUCTS, LLC, Cold Spring Harbor, NY (US)

(72) Inventors: Drew E. O'Connell, Sr., Cold Spring Harbor, NY (US); Nicholas A. Petry, Manchester, VT (US); Lansing M. Lewis, III, Tallahassee, FL (US); Bradley Dean, Lawrenceville, GA (US)

(73) Assignee: CIRRUS HEALTHCARE PRODUCTS, LLC, Cold Spring Harbor, NY (US)

( * ) Notice: Subject to any disclaimer, the term of this patent is extended or adjusted under 35 U.S.C. 154(b) by 83 days.

(21) Appl. No.: 15/199,085

(22) Filed: Jun. 30, 2016

(65) Prior Publication Data

US 2017/0109988 A1  Apr. 20, 2017

Related U.S. Application Data

(63) Continuation-in-part of application No. 15/050,114, filed on Feb. 22, 2016.

(60) Provisional application No. 62/243,756, filed on Oct. 20, 2015.

(51) Int. Cl.
*A61F 11/08* (2006.01)

(52) U.S. Cl.
CPC .................................. *A61F 11/08* (2013.01)

(58) Field of Classification Search
CPC ........................................................ A61F 11/08
See application file for complete search history.

(56) References Cited

U.S. PATENT DOCUMENTS

| | | | |
|---|---|---|---|
| 5,467,784 A | 11/1995 | Mobley | |
| 5,613,222 A | 3/1997 | Guenther | |
| 5,755,234 A * | 5/1998 | Mobley | A61F 11/08 128/864 |
| 5,819,745 A | 10/1998 | Mobley | |
| 2004/0163882 A1* | 8/2004 | Fleming | A61F 11/10 181/135 |
| 2009/0106879 A1 | 4/2009 | Post | |
| 2010/0071708 A1* | 3/2010 | Lenhardt | A61F 11/08 128/868 |

(Continued)

*Primary Examiner* — Charles E Anya
(74) *Attorney, Agent, or Firm* — Ware, Fressola, Maguire & Barber LLP

(57) ABSTRACT

The present invention is directed to a method, apparatus and computer program for provision of meteorological data pertaining to a particular atmospheric condition to assist in the timing of a remedy to ameliorate involuntary physical distress caused by a change in the atmospheric condition. The remedy according to an exemplary embodiment of the present invention may be an earplug including a body having a first end, a second end and a longitudinal axis extending from the first end to the second end, a bore defined within the body and extending from the first end to the second end along the longitudinal axis of the body, and a pressure regulator positioned within the bore and providing an air flow rate of $3.4 \times 10^{-6}$ to $7.8 \times 10^{-5}$ cc/sec through the bore.

34 Claims, 11 Drawing Sheets

(56) References Cited

U.S. PATENT DOCUMENTS

| | | | |
|---|---|---|---|
| 2012/0226111 A1* | 9/2012 | LeBoeuf | A61B 5/0205 |
| | | | 600/301 |
| 2014/0184407 A1* | 7/2014 | Patil | A62B 17/00 |
| | | | 340/539.11 |
| 2014/0316012 A1 | 10/2014 | Freyman | |
| 2015/0082231 A1* | 3/2015 | Ren | G06T 11/60 |
| | | | 715/778 |
| 2015/0092971 A1* | 4/2015 | Kim | H04R 25/558 |
| | | | 381/328 |
| 2016/0089087 A1* | 3/2016 | Iseberg | A61B 5/7203 |
| | | | 600/559 |
| 2016/0292988 A1* | 10/2016 | McCleary | G08B 21/14 |

* cited by examiner

EQUAL PRESSURE IN EXTERNAL EAR CAVITY AND MIDDLE EAR

GREATER PRESSURE IN MIDDLE EAR THAN EXTERNAL EAR CAVITY CAUSES PAIN

METHOD, APPARATUS AND COMPUTER PROGRAM FOR PROVISION OF METEROLOGICAL DATA TO ASSIST IN TIMING OF REMEDY TO AMELIORATE PHYSICAL DISTRESS

CROSS-REFERENCE TO RELATED APPLICATIONS

This application claims priority to U.S. Provisional Appl. No. 62/243,756 filed Oct. 20, 2015, and is a continuation-in-part of U.S. appl. Ser. No. 15/050,114 filed Feb. 22, 2016, which also claimed priority to U.S. Provisional Appl. No. 62/243,765 filed Oct. 20, 2015, and which are all hereby incorporated by reference in their entireties.

BACKGROUND OF THE INVENTION

1. Field of the Invention

The present invention relates to exemplary embodiments of a method, apparatus and computer program for provision of meteorological data to assist in timing of remedy to ameliorate physical distress. More particularly, the present invention is directed to a method, apparatus and computer program configured to provide meteorological data in order to allow a user to employ a preemptive and/or corrective measure, such as a migraine relief earplug, in response to a particular atmospheric condition, such as a change in barometric pressure, to ameliorate physical distress that has been caused or may be caused by such particular atmospheric condition.

2. Description of Related Art

The middle ear is an air-filled cavity that connects to the outside environment via the Eustachian tube. Under normal conditions, there is no difference between the air pressure in the outside environment and the middle ear. This condition is illustrated in FIG. 1 which is a schematic drawing of the ear, and shows that under normal conditions there is no pressure difference across the eardrum. However, when there is a change in air pressure, such as when there is a change in barometric pressure due to weather conditions, change in elevation, etc., there is a difference in the air pressure between the middle ear and the outside environment. Under conditions in which such a pressure differential exists, the Eustachian tube acts as a valve between the outside environment and the middle ear. In this capacity, the Eustachian tube opens for a fraction of a second in response to swallowing or yawning, allowing airflow through it so that the pressure differential between the outside environment and the middle ear equilibrate.

During a decrease in barometric pressure the air pressure in the outside environment, that is, the environment outside the middle ear, is less than that of the pressure inside the middle ear. Under these conditions, the positive relative pressure in the middle ear forces air out of the Eustachian tube thereby lowering the pressure inside the middle ear to the same pressure as the outside environment. If the Eustachian tube is blocked, as described more fully below, the positive pressure in the middle ear applies pressure to the ear drum, as shown schematically in FIG. 2, causing it to bow outward toward the external ear cavity.

Conversely, during an increase in barometric pressure, the air pressure in the outside environment is greater than that of the pressure inside the middle ear. Under these conditions, the negative relative pressure in the middle ear causes airflow from the outside environment through the Eustachian tube and into the middle ear, thereby increasing the pressure inside the middle ear to the same pressure as the outside environment. Again, under condition in which the Eustachian tube is blocked, the negative pressure in the middle ear causes deformation of the ear drum, bowing it inward toward the middle ear, as shown schematically in FIG. 9.

Under normal circumstances, when there is no or little blockage of the Eustachian tube, as the pressure differential increases across the ear drum between the middle ear and outside environment, voluntary swallowing and/or chewing releases the pressure through the Eustachian tube.

A barometric pressure headache is a type of migraine headache that is caused by a change in atmospheric air pressure and is characterized by a pounding headache centered on the front of the head and sinus area. Approximately 72% of migraines are related to barometric pressure changes. Barometric pressure is the weight of air pressing against the Earth, and is called barometric pressure because such pressure is measured by barometers. Barometric pressure can be affected by weather, in that an approaching storm causes barometric pressure to drop, which is usually when a barometric pressure headache will form. Some treatments include taking pain medication and taking steps to counteract the pressure change by lowering blood pressure. Barometric changes generally range from 31 inches of mercury to 29 inches of mercury with a base pressure of 29.92. The psi differential for sea level barometric pressure reading at the high and low readings is 0.982 psi. While moving from sea level to a much higher altitude, e.g. hiking, skiing, flying when barometric pressure is high will greatly increase the psi change as a result of gaining altitude. However, when not changing altitude, the pressure differential between potential high and low barometric pressures is small. Even though this pressure differential may be relatively small, it may still be significant enough to induce barometric pressure headaches. Therefore, what is needed is a means for reducing the severity of pain and duration of pain associated with barometric pressure headaches.

While prior devices, such as the earplugs discussed in U.S. Pat. No. 5,467,784, which is hereby incorporated by reference in its entirety, provide for pressure regulation of the ear canal, such prior devices are intended for rapid changes in pressure associated with commercial air travel. These prior devices do not provide sufficient adaptation when the barometric pressure changes are relatively small or slow to occur. Furthermore, these prior devices are used for short periods of time due to the rapid changes in pressure associated with such activities as commercial air travel, but are generally not suitable for long durations of use.

Therefore, what is needed in order to provide for the reduction of the severity of pain and duration of pain associated with a barometric pressure headache is an earplug that provides for reducing the speed at which the earplug allows the pressure on the ear drum to be equitized, and can be comfortably worn for long period of time. It would also be advantageous to provide a means for notifying a user when such an earplug should be implemented by the user.

SUMMARY OF THE INVENTION

The present invention contemplates the provision of a method, apparatus and computer program for provision of meteorological data pertaining to a particular atmospheric condition to assist in the timing of a remedy to ameliorate involuntary physical distress caused by a change in the atmospheric condition. The remedy according to an exemplary embodiment of the present invention may be earplug that provides for regulated flow of air through the earplug to allow for mitigation of the effects caused by gradual barometric pressure changes when the earplug is installed in a person's ear canal and is sufficiently comfortable so as to be worn for long enough durations during the gradual barometric pressure changes.

It is an object of the present invention to provide a method of using an earplug in the treatment and/or prevention of barometric pressure headaches.

It is further an object of the present invention to provide an earplug and a method of using such earplug to counteract the effects of barometric pressure changes, such as the effects of barometric pressure headaches caused from barometric pressure changes.

It is still another object of the present invention to provide an application that provides a user of the earplug a notification of impending or occurring atmospheric changes that would warrant the use of the earplug.

It is yet another object of the present invention to provide an earplug and a method of using such earplug that reduces the severity of pain and duration of pain caused by a barometric pressure headache. It is a further object of the present invention to provide a method of informing the user of the earplug that may suffer from barometric pressure headaches of impending or occurring barometric pressure changes that would warrant the use of the earplug.

It is still another object of the present invention to provide an earplug and a method of using such earplug that also is configured to allow for sound attenuation to further help with mitigating headache discomfort.

It is yet another object of the present invention to provide an earplug that is configured to be comprised of a soft material, such as silicone, in order to be comfortable enough to be worn for long periods of time, e.g. 3 to 24 hours, but resilient enough to still perform the functions associated with a headache relief earplug.

It is an object of this invention to regulate the rate of airflow through an ear plug when it forms an air tight pressure seal in the ear canal.

It is a further object of this invention to reduce the rate of pressure change in an external ear canal to reduce the pain and discomfort caused by pressure differences across the ear drum, such as the pain and discomfort caused by a barometric pressure headache.

According to an exemplary embodiment of the present invention a method is provided that includes receiving a signal over a network connection from a device of a user requesting meteorological data pertaining to a particular atmospheric condition, the user requesting the meteorological data to assist the user in timing of a remedy to ameliorate involuntary physical distress in the user caused by a change in the atmospheric condition, determining a current geographic location or an associated geographic location of the user device, retrieving meteorological data subsisting and forecast at the determined geographic location, and sending a response signal over the network connection to the user device, the response signal having the meteorological data subsisting and forecast at the determined geographic location including at least the particular atmospheric condition organized for presentation over a selected time frame so that the timing of the remedy is ascertainable in case the atmospheric condition is forecast to change in such a way as to cause the involuntary physical distress in the user.

According to this or other exemplary embodiments of the present invention, the particular atmospheric condition is barometric pressure.

According to this or other exemplary embodiments of the present invention, the remedy to ameliorate the involuntary physical distress caused by the change in the barometric pressure comprises at least one earplug having a body having a first end, a second end and a longitudinal axis extending from the first end to the second end, a bore defined within the body and extending from the first end to the second end along the longitudinal axis of the body, and a pressure regulator positioned within the bore and providing an air flow rate of $3.4 \times 10^{-6}$ to $7.8 \times 10^{-5}$ cc/sec through the bore.

According to this or other exemplary embodiments of the present invention, the pressure regulator of the earplug is comprised of a porous material having a porosity of 1.3 to 2 microns.

According to this or other exemplary embodiments of the present invention, the meteorological data in the response signal is organized for presentation on the user device as a chart of the meteorological data subsisting and forecast at the determined geographic location including at least the particular atmospheric condition organized for presentation over the selected time frame.

According to this or other exemplary embodiments of the present invention, the chart indicates when to initiate the remedy by a graphical indication of a threshold such that the timing of the remedy is prescribed upon the meteorological data crossing the threshold.

According to this or other exemplary embodiments of the present invention, the change in the barometric pressure is an increase in the barometric pressure, a decrease in the barometric or the barometric pressure meeting a certain predefined threshold level.

According to this or other exemplary embodiments of the present invention, the forecast alerts the user a selected number of hours in advance of likely changes in the particular atmospheric condition.

According to this or other exemplary embodiments of the present invention, the response signal received over the network connection to the user device includes an indication of when to initiate insertion of the at least one earplug into the user's ear canals.

According to this or other exemplary embodiments of the present invention, an apparatus is provided that may include at least one processor, and at least one storage device including a computer program, the at least one storage device and the computer program configured to, with the at least one processor, cause the apparatus to carry out the exemplary method according to various aspects of the present invention.

According to another exemplary embodiment of the present invention, a method is provided that includes sending a request signal over a network connection from a device of a user requesting meteorological data pertaining to a particular atmospheric condition, the user requesting the meteorological data to assist the user in timing of a remedy to ameliorate involuntary physical distress in the user caused by a change in the particular atmospheric condition, request signal including a current geographic location or an associated geographic location of the user device, and receiving a response signal over the network connection to the user device, the response signal having the requested meteorological data subsisting and forecast at the geographic location including at least the particular atmospheric condition organized for presentation over a selected time frame so that the timing of the remedy is ascertainable in case the atmospheric condition is forecast to change in such a way as to cause the involuntary physical distress in the user.

According to this or other exemplary embodiments of the present invention, a nontransitory computer readable medium is provided that may have a computer program stored thereon that is executable by a processor for causing a portable electronic display device to carry out the exemplary method according to various aspects of the present invention.

According to this or other exemplary embodiments of the present invention, an apparatus is provided that may include at least one processor and at least one memory including an application that is executable by the at least one processor to cause the apparatus at least to carry out the exemplary method according to various aspects of the present invention.

According to this or other exemplary embodiments of the present invention, the particular atmospheric condition is barometric pressure.

According to this or other exemplary embodiments of the present invention, the remedy to ameliorate the involuntary physical distress caused by the change in the barometric pressure comprises at least one earplug having a body having a first end, a second end and a longitudinal axis extending from the first end to the second end, a bore defined within the body and extending from the first end to the second end along the longitudinal axis of the body, and a pressure regulator positioned within the bore and providing an air flow rate of $3.4 \times 10^{-6}$ to $7.8 \times 10^{-5}$ cc/sec through the bore.

According to this or other exemplary embodiments of the present invention, the pressure regulator of the earplug is comprised of a porous material having a porosity of 1.3 to 2 microns.

According to this or other exemplary embodiments of the present invention, the meteorological data in the response signal is organized for presentation on the user device as a chart of the meteorological data subsisting and forecast at the determined geographic location including at least the particular atmospheric condition organized for presentation over the selected time frame.

According to this or other exemplary embodiments of the present invention, the chart indicates when to initiate the remedy by a graphical indication of a threshold such that the timing of the remedy is prescribed upon the meteorological data crossing the threshold.

According to this or other exemplary embodiments of the present invention, the response signal received over the network connection to the user device includes an indication of when to initiate insertion of the at least one earplug into the user's ear canals.

Furthermore, the headache relief earplug of the present invention may be designed to make an air tight seal in the external ear canal and to regulate the rate of change in air pressure between the external ear canal and the middle ear when a user is exposed to changes in barometric atmospheric pressure. By so doing, the plug can delay the build-up of an air pressure differential between the external ear canal and the middle ear, which are separated by the ear drum. As a result, the user, even with a partially blocked Eustachian tube, has an extended period of time to equalize the barometric pressure differential between the middle ear and the external environment. Normally, these differentials are equalized by the Eustachian tube, which vents the middle ear into the throat. The pressure regulating ear plug creates an enclosed environment between the outside environment and the ear drum. Over time, the headache relief earplug slowly leaks air into or out of the volume immediately exterior to the ear drum, so that the pressure in said volume equilibrates with the pressure outside of the earplug. This delay increases the time available for the Eustachian tube to perform its function of equilibrating the middle ear pressure with the pressure in the external environment.

The headache relief earplug controls the rate at which the barometric pressure changes in the external ear canal adjacent the ear drum. The Eustachian tube then has more time to respond to the pressure changes thereby reducing discomfort. The amount of additional time the Eustachian tube has depends on the porosity of the regulating element inside the ear plug the ear plug of the present invention is an elongated tube of the type typically used for sound attenuation, with a slow leak porous medium disposed within the tube. Examples of such porous media include porous metal material and porous ceramic material, and the ceramic material is the presently preferred material for pressure regulation. Thus, the system can increase substantially the time required to equalize the pressure in the ear canal to the pressure in the environment in which the user is subjected. Air flow preferred for this application of barometric pressure change control is projected to be $3.4 \times 10^{-6}$-$7.8 \times 10^{-5}$ cc/sec. The filter porosity for the pressure regulating device used with the headache relief earplug according to an exemplary embodiment of the present invention may preferably be 1.3-2 microns.

The present invention is also effective for the purpose of sound attenuation by default being a blockage in the ear canal and absorbing sound waves as they enter the ear canal. This is an added benefit to the plugs use in mitigating the intensity of a barometric pressure headache.

In accordance with another exemplary aspect of the present invention, the material used for forming the headache relief earplug may be comprised of a soft yet resilient material, for example a soft molded silicone. Preferably, the soft molded silicone may have a durometer between 60 and 64 on the OO scale.

Both sound attenuation and comfort of the headache relief earplug due to its construction with a soft material may also help to mitigate headache discomfort if the headache has already begun.

BRIEF DESCRIPTION OF THE SEVERAL VIEWS OF THE DRAWINGS

For a fuller understanding of the nature and object of the present invention, reference should be had to the following detailed description taken in connection with the accompanying drawings, in which.

DETAILED DESCRIPTION OF THE INVENTION

The present invention now will be described more fully hereinafter with reference to the accompanying figures, in which exemplary embodiments of the invention are shown. The invention may, however, be embodied in many different forms and should not be construed as limited to the embodiments set forth herein.

Figure 1:
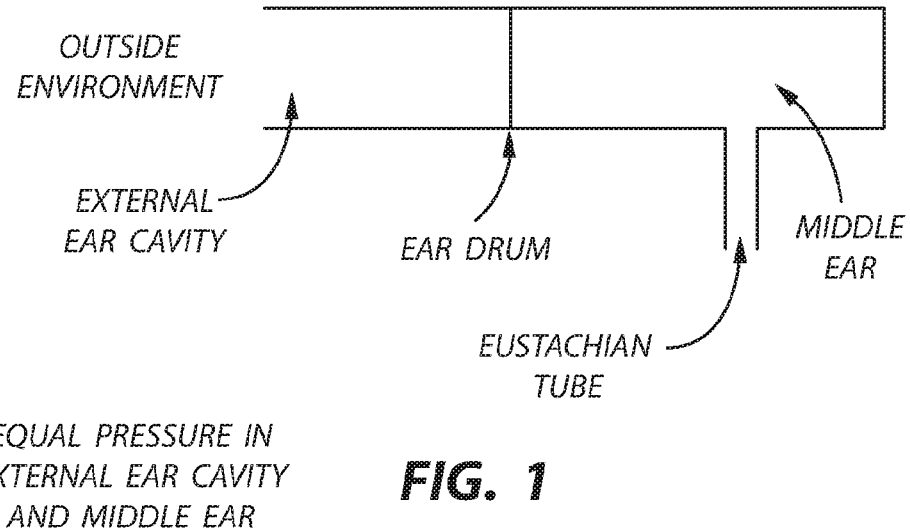
FIG. 1 is a schematic view of an ear in which there is no pressure differential between the external environment and the middle ear.
Figure 2:
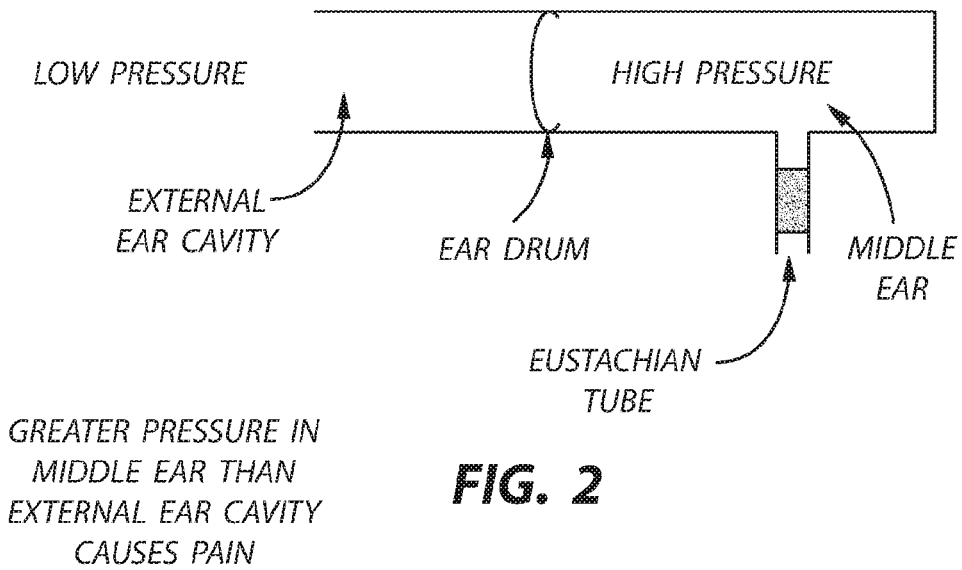
FIG. 2 is a schematic view of an ear in which there is a pressure differential between the external environment and the middle ear wherein the pressure in the middle ear is greater than the pressure in the external environment, and wherein the Eustachian tube is blocked.
Figure 1A:
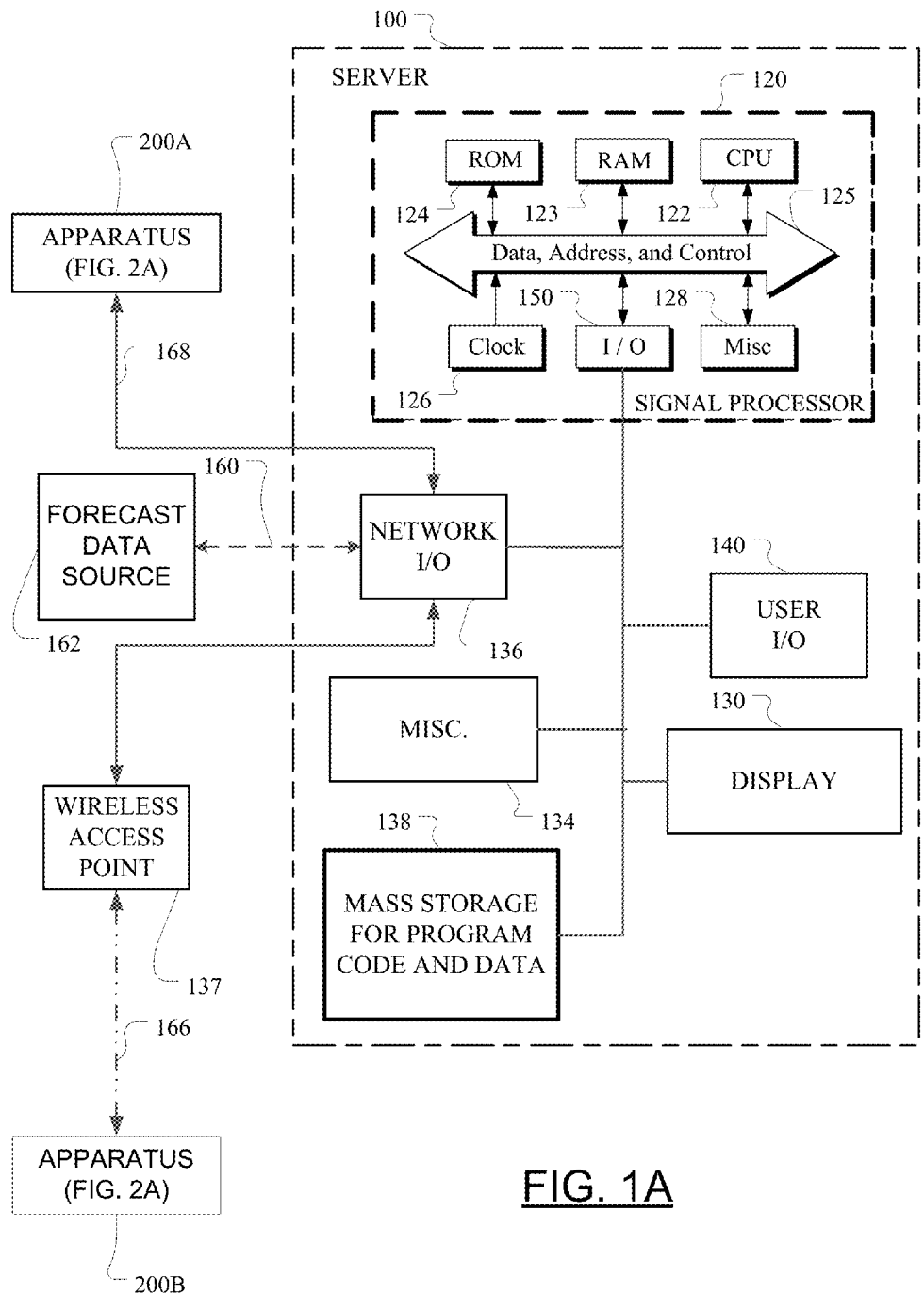
FIG. 1A shows an exemplary embodiment of a system according to the teachings hereof.

FIG. 1A shows an embodiment of a system according to the teachings hereof. As shown, the system may include a server 100 that may for instance be a single unit or may instead have its operative functions distributed among various units. As shown, it may contain a signal processor 120 with a central processing unit (CPU) 122, random access memory (RAM) 123, read-only memory (ROM) 124, a clock 126, miscellaneous hardware, firmware, and software 128, as well as an input/output (I/O) port 150 connected to data, address and control lines 125. The I/O port 150 permits communication between the signal processor 120 and devices outside the signal processor that are shown interconnected by a bus within the server 100. Thus, the I/O port 150 may be connected by various signal lines (shown as a single common signal line or bus) interconnecting various devices such as a display 130, miscellaneous hardware 134, network I/O 136, user I/O 140, and mass storage 138 for computer program code and meteorological data. The network I/O may be connected by one or more hardwired or wireless connection lines 160 to other parts of the system such as a weather forecast data source 162 for providing up-to-date meteorological data and forecasts thereof. The source 162 of meteorological data may for instance be made available to the server by an independent vendor for an access fee. Other type of data such as location information may likewise be made available for instance by checking the IP address of an apparatus 200A, 200B communicating with the server and making a geographic location determination based on that. In any event, the apparatus 200A, 200B may be responsive to a forecast information signal from the server provided for instance by the forecast data source 162 via the network I/O 136 based on a determined location of the apparatus 200A, 200B. In order to minimize accesses by the server to the forecast data source 162, a given apparatus 200A, 200B may be grouped by location such as a circumscribed region within which the forecast will generally be similar or the same. As shown, the network I/O 136 may be connected to a wireless access point 137 that provides wireless access such as shown by a wireless connection line 166 to an apparatus 200B that may take the form such as shown by the apparatus 200 of FIG. 2, e.g., in the form of a portable wireless device in the possession of a user.

Figure 1B:
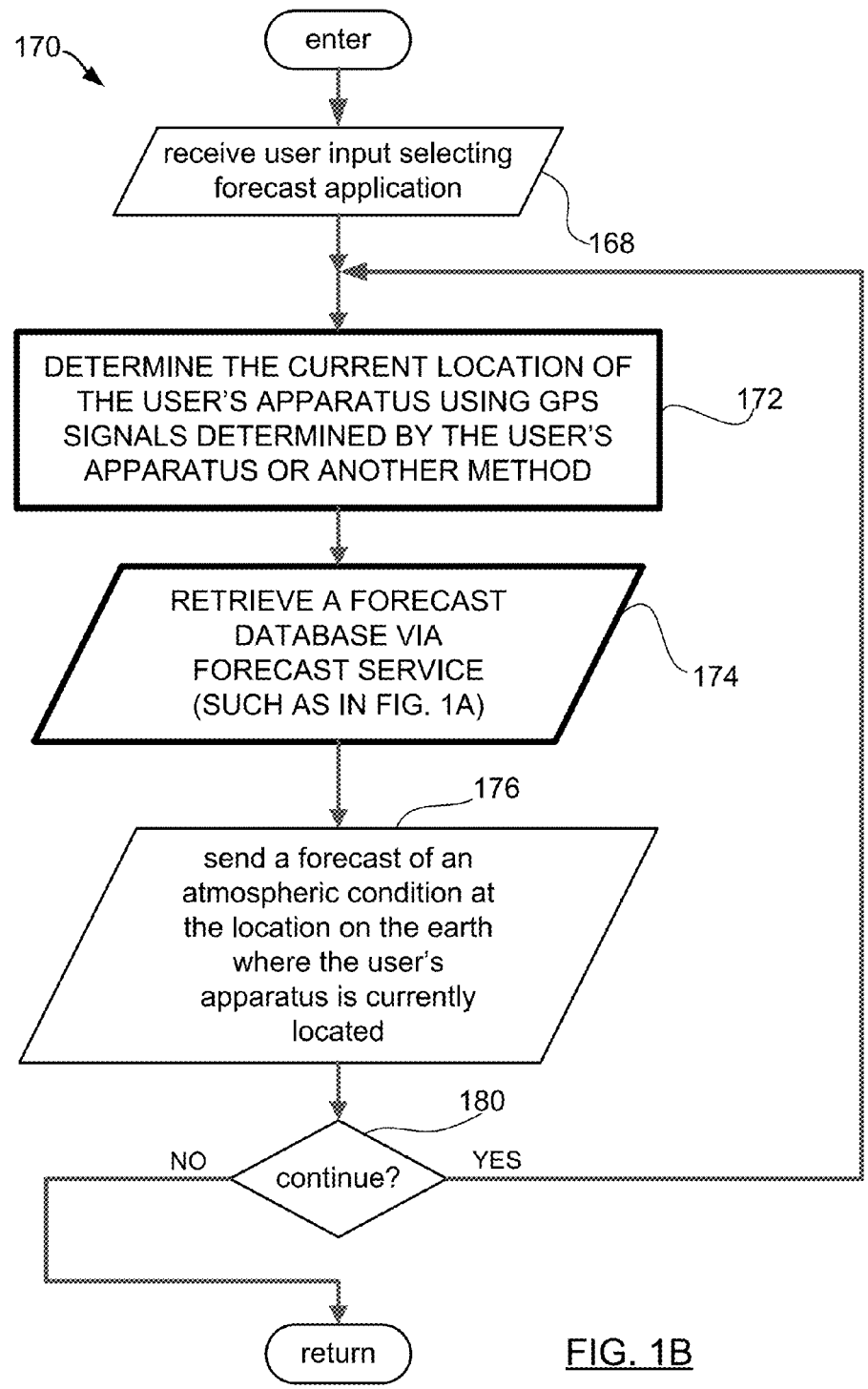
FIG. 1B is an exemplary flowchart that shows the server of FIG. 1A in operation, according to the teachings hereof.

In operation, as shown by a step 168 in a flow chart 170 in FIG. 1B, the server 100 receives a signal over a network connection 166, 168 from an apparatus such as a device 200A, 200B of a user requesting meteorological data pertaining to a particular atmospheric condition, the user requesting the meteorological data to assist the user in timing of a remedy to ameliorate involuntary physical distress in the user caused by a change in the atmospheric condition. Upon receipt, the server 100 determines a current geographic location or an associated geographic location of the user device 200A, 200B as shown by a step 260. The user's apparatus may make this determination and send a determined location to the server along with the request. This may for instance be done by use of a Global Positioning System (GPS) tracker in the user's apparatus. Such a determination may be done in the user's device or the user device may send raw GPS satellite signaling data so that the determination is made by the server. Other methods such as inferring the geographic location from an IP address of the user's apparatus or by triangulation between the user's apparatus and several wireless access points. Once the geographic location is determined in the step 172, the server retrieves meteorological data subsisting and forecast at the determined geographic location as shown by a step 174. The retrieval may be carried out by retrieval from the mass storage device 138 or by accessing the forecast service 162 via the network I/O 136. As shown in a step 176, the server then sends a response signal over the network connection to the requesting user apparatus 200A, 200B, the response signal having the meteorological data subsisting and forecast at the determined geographic location including at least the particular atmospheric condition. The data may be organized for presentation over a selected time frame so that the timing of the remedy is ascertainable in case the atmospheric condition is forecast to change in such a way as to cause the involuntary physical distress in the user.

The forecast may be presented to alert the user a selected number of days in advance of possible changes in the particular atmospheric condition. Or, the forecast may be presented to alert the user a selected number of hours in advance of likely changes in the particular atmospheric condition. The meteorological data in the response signal may be organized for presentation on the user device as a chart of the meteorological data subsisting and forecast at the determined geographic location including at least the particular atmospheric condition organized for presentation over the selected time frame. In that case, the chart may indicate when to initiate the remedy by a graphical indication of a threshold such that the timing of the remedy is prescribed upon the meteorological data crossing the threshold. Or, the meteorological data in the response signal may be formatted for presentation on the user device as tabular data. The request signal received by the server over the network from the user device may include an indication of a requested granularity of the meteorological data to be sent by the server to the requesting user apparatus in the response signal. The particular atmospheric condition may for instance be barometric pressure.

Although the server 100 has been presented as including at least one processor 120 and at least one storage device 138 including a computer program and data, the at least one storage device and the computer program configured to, with the at least one processor, cause the server 100 to carry out the above described method, it should be realized that the system shown in FIG. 1A can take different forms in actual hardware including hardware distributed in different locations. FIG. 1A thus shows merely an example of a system, according to an embodiment. The various modules shown may include at least one signal processor that includes at least one central processing unit and at least one memory device including a computer program that executes, at least in part, the processing described above. These processes may be expressed as a combination of computer instructions and data definitions that enable a computer such as a central processing unit to perform acts of computation or control. Thus, such instructions may take the form of software modules such as image and data processing modules as outlined in FIG. 1A. Such software is sometimes referred to as comprising computer program code that likewise comprises computer instructions and data definitions expressed in a programming language or in a form output by an assembler, compiler, or other translator. A system comprising computer program code is thus able, together with at least one central processing unit, to cause the system at least to carry out certain process steps such as outlined in whole or in part above. The methods shown herein may be coded by a computer programmer so as to express method steps in a programming language. The foregoing considerations apply equally to the various hardware and methods shown by way of example below.

Figure 2A:
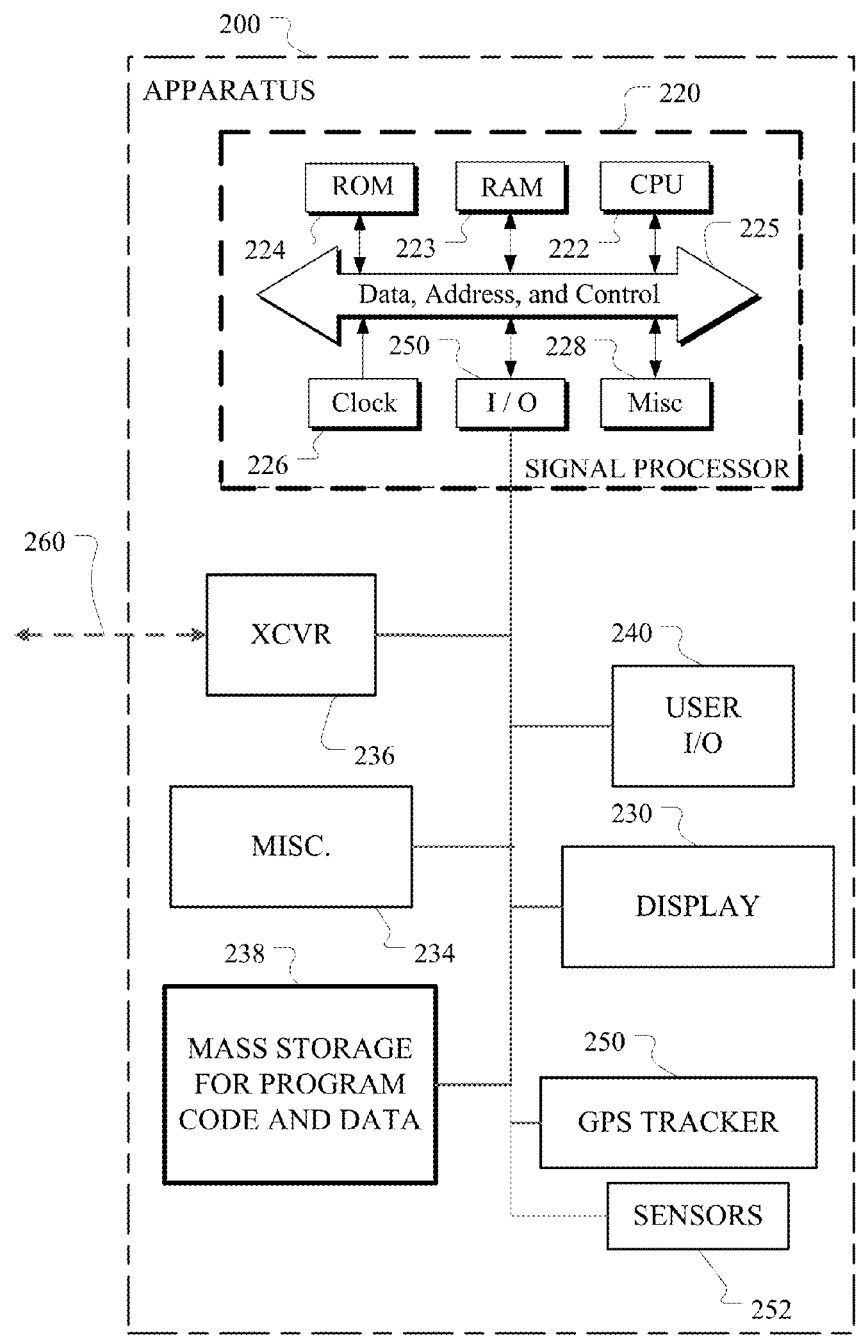
FIG. 2A shows an embodiment of an apparatus of a user in the system of FIG. 1A, according to the teachings hereof.
Figure 2B:
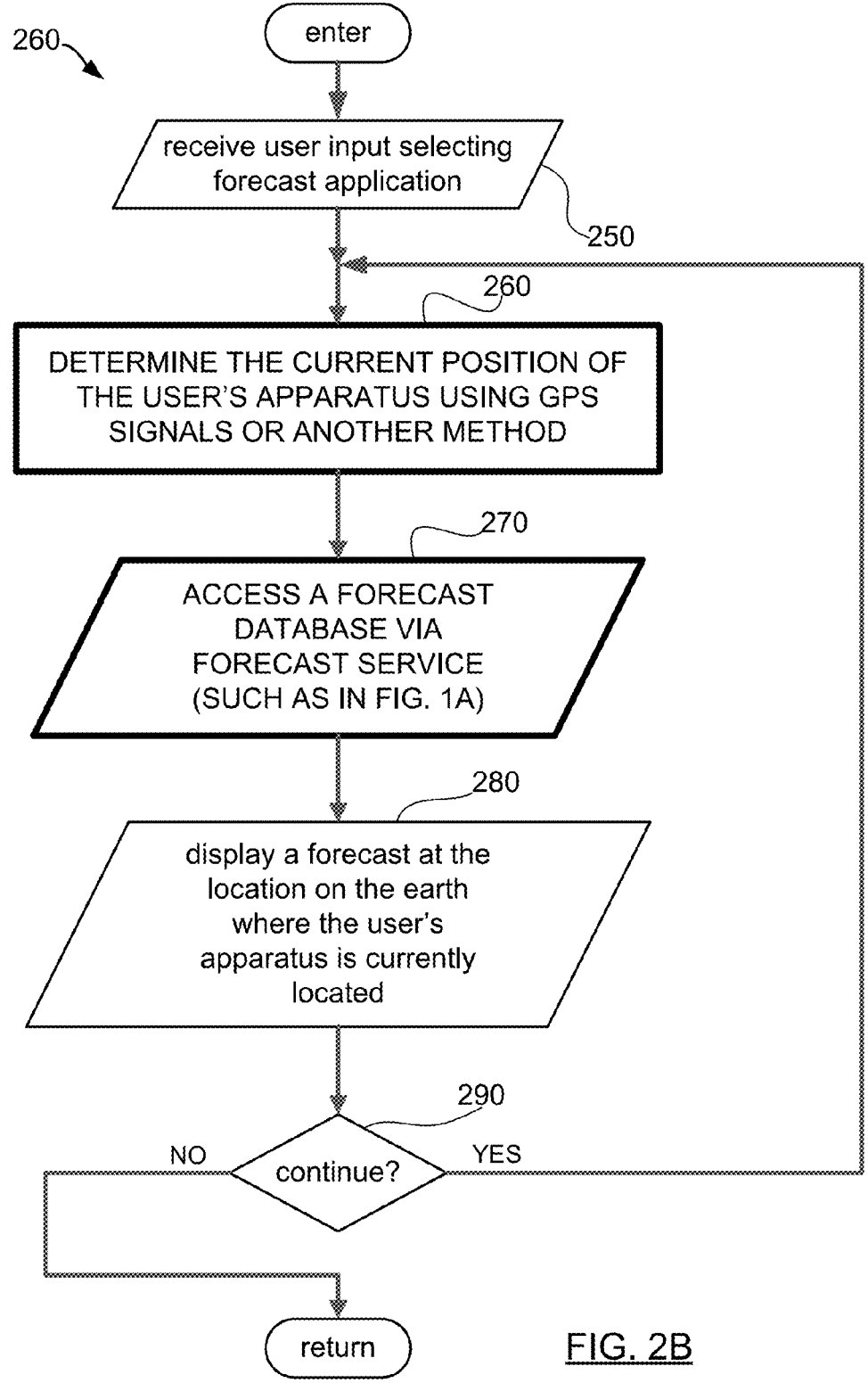
FIG. 2B is an exemplary flowchart that shows the user apparatus of FIG. 2A in operation, according to the teachings hereof.

FIG. 2B shows an example of a method 260, according to an embodiment, carried out on an exemplary apparatus 200 as shown in FIG. 2A. The apparatus 200 may include at least one signal processor 220 that includes at least one central processing unit (CPU) 222 and at least one memory device 224 including computer program code configured to, with the at least one central processing unit, cause the apparatus at least to carry out certain steps. In an exemplary embodiment, such an apparatus 200 may be a portable electronic display device such as a tablet handled by a user at a certain location on the surface of the earth, e.g., at a certain latitude and longitude. Such an exemplary portable electronic display device 200 may include a user input interface arrangement such as shown as a user input/output device 240 that is responsive to receiving a user input. Such a user input might be made by a finger or stylus touching a touch sensitive screen surface (touchscreen) of a display 230. Thus, as shown in a step 250 in FIG. 2B, the user input device 240 of the exemplary apparatus 200 of FIG. 2A may receive and condition the sensed touch input and send a signal to the signal processor 220 that includes the above mentioned at least one CPU 222 and the at least one memory device 224. The received touch input from the user may be a selection of a forecast application displayed as an icon on the screen of the display 234 of the exemplary portable electronic display device 200. When the portable electronic display device is held in the hand or hands of the user, the screen is visible to the user and forecast imagery may be presented via the forecast application so as to be viewable by the user. In response to the user input, a forecast application launch signal may be generated by the signal processor 220. If the forecast application is stored on the Read Only Memory (ROM) 224, the forecast application launch signal may be used internally within the signal processor 220 to launch the forecast application. Or, it could be transmitted to a memory device 238 that may have the executable code for the forecast application stored in whole or in part therein. The launch of the forecast application causes the forecast application to be presented on the display 230. In an embodiment, it may then prompt the user to input other information concerning details of the desired forecast such as a particular atmospheric condition or a presentation format desired by the user for display.

In operation, as shown by a step 250, the user apparatus 200 receives user input selecting the forecast application. A step 260 may then be performed to determine the current geographic location of the apparatus 200, for instance using the GPS tracker 210. The GPS tracker 210 is responsive to radio signals from a plurality of geo stationary satellites. The GPS tracker 210 by itself or the tracker in conjunction with the signal processor 220 is able to determine the position of the apparatus 200. More generally, since other nations have similar satellite systems, such a tracker may include a GNSS (Global Navigation Satellite System) antenna, a GNSS band pass filter (BPF), a temperature compensated crystal oscillator, and a GNSS Integrated Circuit (IC) that, may for instance be a combination GPS/GLONASS/Bluetooth/FM IC or an equivalent stand-alone GPS/GLONASS IC. The antenna may be a planar inverted-F antenna (a micro-strip built using a trace on a printed circuit board). An RF section may include a low noise amplifier (LNA), mixer, synthesizer, and intermediate frequency (IF) filter. A baseband section may include an acquisition engine, tracking channels, and a microprocessor. In a home or office environment it is also possible to use WiFi positioning. Other methods of determining the location are possible as mentioned above.

As shown in a step 270, a request signal may be sent over a network connection 166, 168 from the apparatus of the user that requests meteorological data pertaining to a particular atmospheric condition. The user requesting the meteorological data needs assistance in timing a remedy to ameliorate involuntary physical distress in the user caused by a change in the particular atmospheric condition. The request signal sent to the server may include a current geographic location or an associated geographic location of the user device. The server then carries out the methodology shown in FIG. 1B, or similar, before sending a response signal over the network connection to the user apparatus as indicted by a step 280 in FIG. 2B. The response signal is received by the user apparatus having the requested meteorological data subsisting and forecast at the determined geographic location including at least the particular atmospheric condition organized for presentation, as shown in a step 280, over a selected time frame so that the timing of the remedy is ascertainable in case the atmospheric condition is forecast to change in such a way as to cause the involuntary physical distress in the user. A nontransitory computer readable medium such as the ROM 224 or the mass storage device 238 may have a computer program stored thereon that is executable by the signal processor 220 for causing the apparatus 200 (such as a portable electronic display device) to carry out a method such as shown FIG. 2B for instance as an "app" downloadable from an app store. Thus the apparatus 200 may be understood as a product including at least one processor 220 and at least one memory 224, 223, 238 including an application that is executable by the at least one processor to cause the apparatus 200 at least to carry out a method such as shown in FIG. 2B.

As suggested previously, although the server 100 has been presented as including at least one processor 120 and at least one storage device 138 including a computer program and data, and that the at least one storage device and the computer program are configured to, with the at least one processor, cause the server 100 to carry out the above described method, it should be realized that the teachings hereof may be carried out with various modifications of the disclosed method using various combinations of hardware and software, for instance in a distributed way.

Figure 3:
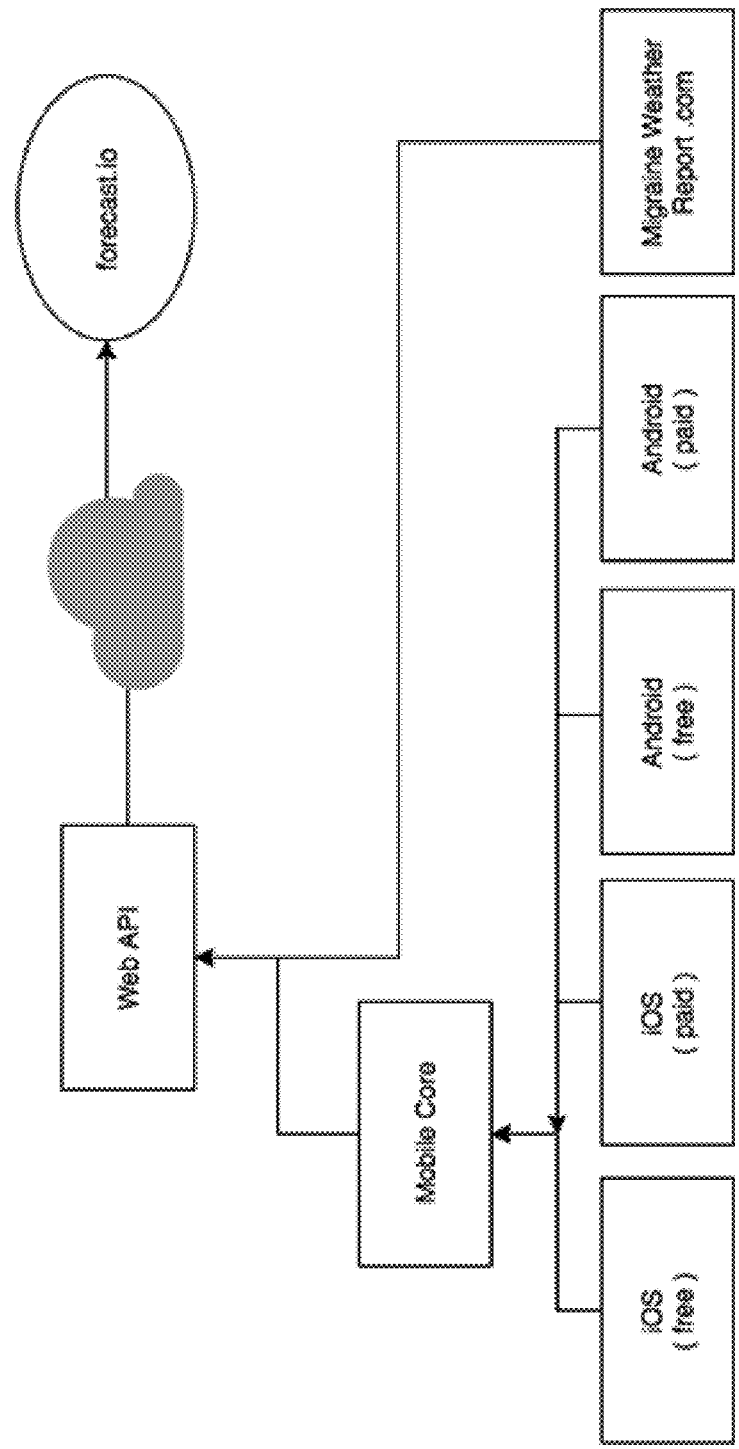
FIG. 3 shows an "app" architecture and platform according to the teachings hereof.

For example, the particular atmospheric condition may be barometric pressure, an "app" may be developed to target migraine sufferers. A framework for such an "app" is shown in FIG. 3 with the majority of the code in the Web API and Mobile.Core layers:

Back end service
C# ASP.Net WebAPI
running on Microsoft Azure
Mobile applications
Xamarin.Forms
MigraineWeatherReport.com
Angular.js
MigraineWeatherApp.com
Static HTML As will be recognized by developers with Microsoft stack experience, by Certified Xamarin Mobile Developers, and by Microsoft Technology Specialists, the flexibility of the architecture shown in FIG. 3 permits different mobile apps and websites to be built using the same code and framework. The only thing that needs to be changed is the name of the app and the marketing approach taken for the particular type of data and discomfort being targeted. Various diseases, like migraines, are affected for instance by barometric pressure, such as fibromyalgia, rheumatoid arthritis, and joint pain. It should be understood that the particular atmospheric condition chosen for illustration is barometric pressure and the disease is migraine headache but the subject matters disclosed herein are not limited thereto.

In accordance with an exemplary embodiment of the present invention, the remedy to ameliorate involuntary physical distress in the user caused by a change barometric pressure may be a headache relief earplug. An exemplary embodiment of the present invention is illustrated schematically in FIGS. 10 and 11. FIG. 11 is a schematic illustration of the operation of the headache relief earplug of the present invention under conditions comparable to those of FIG. 2, except for the use of the exemplary embodiment of the headache relief earplug according to the present invention. More specifically, FIG. 11 depicts the effect of a decrease in barometric pressure. In FIG. 11, the outside environment has a lower barometric pressure, for example 29 inches of mercury or lower (14.243 Psia or less), than the pressure inside the middle ear 28, which is still at the barometric pressure, for example 29.92 to 31 inches of mercury (14.695 to 15.225 Psia), before the decrease of barometric pressure. The pressure inside the middle ear is a result of the middle ear being pressurized and filled with air prior to the decrease in barometric pressure, and not being able to equilibrate to the current ambient pressure because the Eustachian tube 26 is blocked, schematically depicted at 27, so that the air in the middle ear 28 cannot escape through the Eustachian tube, or at least not at the desired rate sufficient to cause the desired depressurization of the middle ear.

However, because of the installation of the headache relief earplug 24, which is schematically depicted in FIG. 11, the pressure in the volume between the ear drum 20 and the headache relief earplug 24 remains at the prior barometric pressure before the decrease in barometric pressure, and this prior barometric pressure is the same as the pressure in the middle ear. The headache relief earplug 24 is adapted to slowly release air in the volume 30 to the outside environment through the external ear canal 22, and as shown, airflow in direction A illustrated by the arrows occurs. Similarly, provided that there is only partial blockage of the Eustachian tubes, airflow through the blockage 27 travels in the direction depicted by arrow B, so that the pressure in the middle ear equilibrates with the current ambient barometric pressure as it exists in the outside environment.

Figure 9:
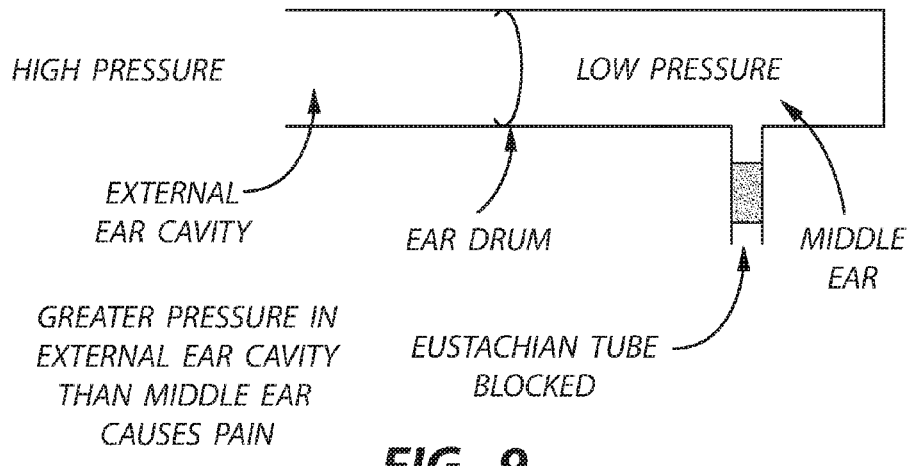
FIG. 9 is a schematic view of an ear in which there is a pressure differential between the external environment and the middle ear wherein the pressure in the middle ear is less than the pressure in the external environment, and wherein the Eustachian tube is blocked.
Figure 10:
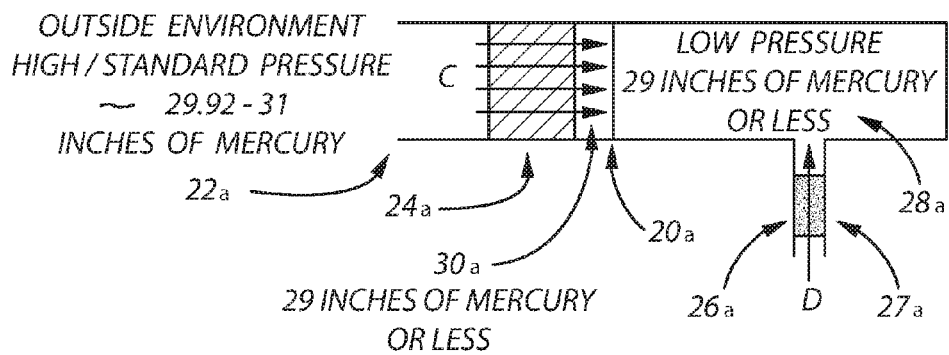
FIG. 10 is a schematic view of an ear in which the headache relief earplug of the present invention is disposed, and in which there is a pressure differential between the external environment and the middle ear, the pressure being less in the middle ear than in the exterior environment, illustrating a change in barometric pressure, and wherein the Eustachian tube is blocked.
Figure 11:
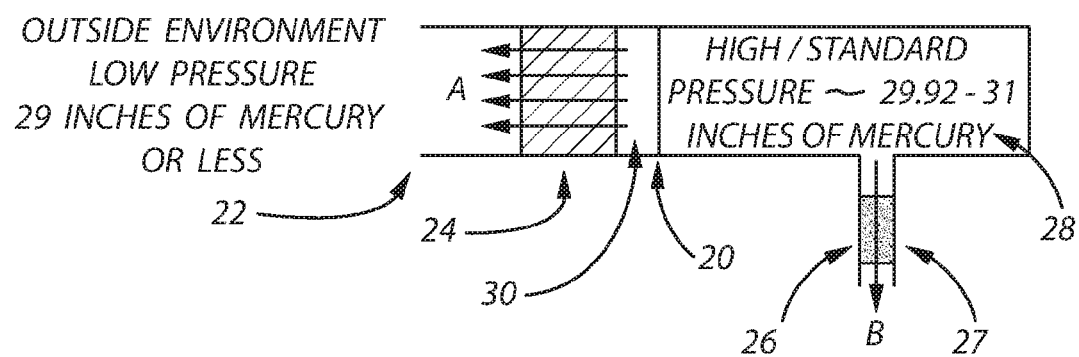
FIG. 11 is a schematic view of an ear in which the headache relief earplug of the present invention is disposed, and in which there is a pressure differential between the external environment and the middle ear, the pressure being greater in the middle ear than in the exterior environment, illustrating a change in barometric pressure, and wherein the Eustachian tube is blocked.

Similarly, FIG. 10 is a schematic illustration of the operation of the headache relief earplug of the present invention under conditions comparable to those of FIG. 9, except for the use of the exemplary embodiment of the headache relief earplug according to the present invention. More specifically, FIG. 10 depicts the effect of an increase in barometric pressure. In FIG. 10, the outside environment has a higher barometric pressure, for example 29.92 to 31 inches of mercury (14.695 to 15.225 Psia), than the pressure inside the middle ear 28a, which is still at the barometric pressure, for example 29 inches of mercury or lower (14.243 Psia or less), before the increase in barometric pressure. The pressure inside the middle ear is a result of the middle ear being pressurized and filled with air prior to the increase in barometric pressure, and not being able to equilibrate to the current ambient barometric pressure of the outside environment because the Eustachian tube 26a is blocked, schematically depicted by blockage 27a, so that the middle ear 28a cannot draw in air through the Eustachian tube, or at least not at the desired rate sufficient to cause the desired pressurization of the middle ear. However, because of the installation of the headache relief earplug 24a, which is schematically depicted in FIG. 10, the pressure in the volume 30a between the ear drum 20a and the pressure regulating earplug 24a remains at the prior barometric pressure before the increase in barometric pressure, and this prior barometric pressure is the same as the pressure in the middle ear. The headache relief earplug 24a is adapted to slowly permit the inflow of air into the volume 30a through the external ear canal 22a and as shown, airflow in direction C illustrated by the arrows occurs. Similarly, provided that there is only partial blockage of the Eustachian tubes, airflow through the blockage 27a travels in the direction depicted by arrow D, so that the pressure in the middle ear equilibrates with the current ambient pressure as it exists in the outside environment.

Figure 12:
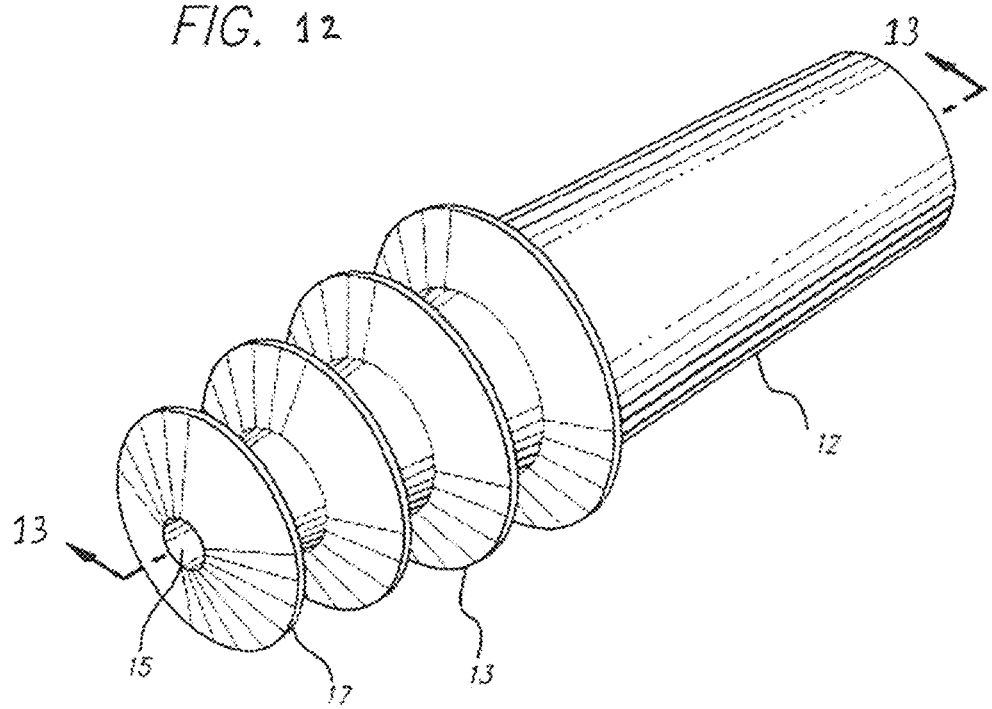
FIG. 12 is a perspective view of an exemplary embodiment of the headache relief earplug according to the present invention.
Figure 13:
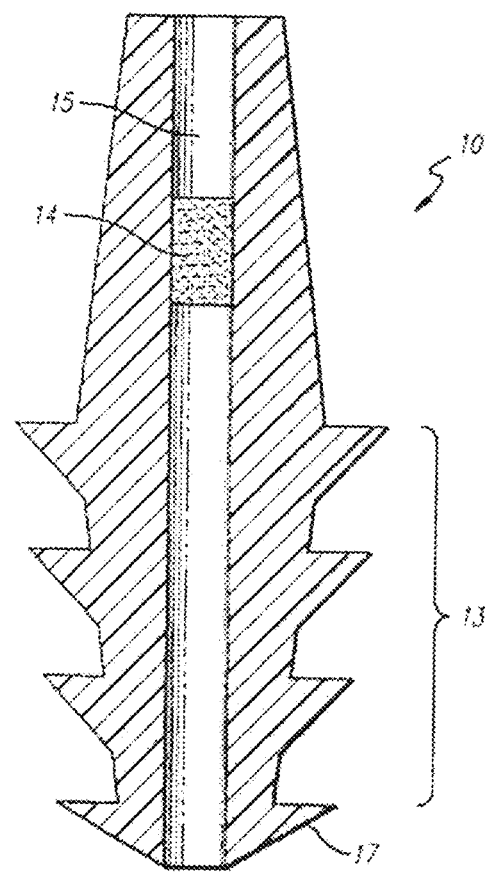
FIG. 13 is a cross-sectional view of the exemplary embodiment of the headache relief earplug according to the present invention taken through line 13-13 of FIG. 12.

An exemplary embodiment of the invention is illustrated in FIGS. 12 and 13. FIG. 13 shows an enlarged cross-sectional view of the exemplary embodiment of the headache relief earplug 10 of the present invention with each of the components identified. The headache relief earplug 10 has a body 12 shaped generally like a conventional sound attenuating ear plug body comprising a ribbed neck section 13 of the headache relief earplug 10. The ribbed neck section 13 provides an air tight seal with the walls of the ear canal when the headache relief earplug 10 is in use. The seal is important to ensure that the pressure regulation is controlled by the pressure regulator 14 and is not affected by a poorly sealed ear plug. There is a bore 15 extending through the headache relief earplug 10 to permit airflow regulated by the pressure regulator 14 therethrough. The pressure regulator 14, which is preferably made of porous metal or porous ceramic, and most preferably, porous ceramic material, permits slow air leakage therethrough, preferably in the range of $3.4 \times 10^{-6}$ to $7.8 \times 10^{-5}$ cc/sec. FIG. 12 shows a perspective view of the subject invention in its preferred embodiment with the plurality of ribs 17 providing a secure and leakage resistant means of retaining the earplug in the ear and preventing any air leakage except through the pressure regulator 14.

The pressure regulator 14 may be made from a porous ceramic material, and the porous ceramic material may preferably be comprised of 73.9% by weight of $Al_2O_3$, 24.6% by weight of $SiO_2$, 0.1% by weight of CaO, 0.1% by weight of MgO, 0.4% by weight of $Fe_2O_3$, 0.4% by weight of $TiO_2$, 0.3% by weight of $K_2O$ and 0.2% by weight of $Na_2O$. The porous ceramic material may also preferably be P-3-C CoorsTek material available from CoorsTek, Inc. of Golden, Colo. The pressure regulator 14 may be made by combining the porous ceramic material with a bonding agent and forming the combination into a small right circular cylinder approximately 0.125 inches (3.18 mm) long with a diameter of 0.083 inches (2.1 mm). Once the cylinder is formed it is heated until the material fuses together and forms the solid pressure regulator 14. The porosity of the ceramic is controlled by adjusting the particle size, bonding agent, and controlling the curing temperature or the heating profile. Preferable, the pressure regulator 14 will have a porosity of between approximately 1.3 and 2 microns. The pressure regulator 14 may then be forced into the bore 15 of the headache relief earplug 10 which has an inside diameter of 0.078 inches (1.98 mm). The interference fit provides an air-tight seal between the pressure regulator 14 ceramic and the bore 15 of the headache relief earplug 10.

The body 12 of the headache relief earplug 10 may be made from any suitable material used for the manufacture and/or construction of earplugs. Preferably, the material used to construct the body 12 should be sufficiently air-tight so that air only passes through the pressure regulator 14, and should also be sufficiently resilient so as to be capable of forming at least a substantially air-tight seal with a user's ear canal. Even more preferably, the material may be a soft molded silicone having a durometer of between about 60 to 64 on the OO scale. It is understood that the OO scale has a spherical radius of 1.20 mm, a diameter of 2.40 mm, an extension of 2.54 mm and a spring force of 113 gf (1.11N).

An exemplary method of using the exemplary headache relief earplug 10 for the treatment of headaches, including barometric pressure headaches, will be discussed with reference to FIGS. 4-8, 12 and 13. The headache relief earplug 10 may be inserted into the ear canal and/or canals of a user, preferably both ear canals of a user, either upon the onset or prior to the onset of the symptoms of a headache. The user of the headache relief earplugs 10 may be aware of impending conditions that may result in the onset of headache symptoms, such as a change in barometric pressure, and the headache relief earplug 10 may be inserted into the user's ear canals to reduce the likelihood of experiencing such symptoms. For example, the user may utilize an "app" according to exemplary embodiments of the present invention discussed above to receive and/or obtain meteorological data related to barometric pressure, which may be the atmospheric condition that induces or contributes to the user's barometric pressure and/or migraine headaches, i.e. the involuntary physical distress of the user.

Figures 4, 5, 6:
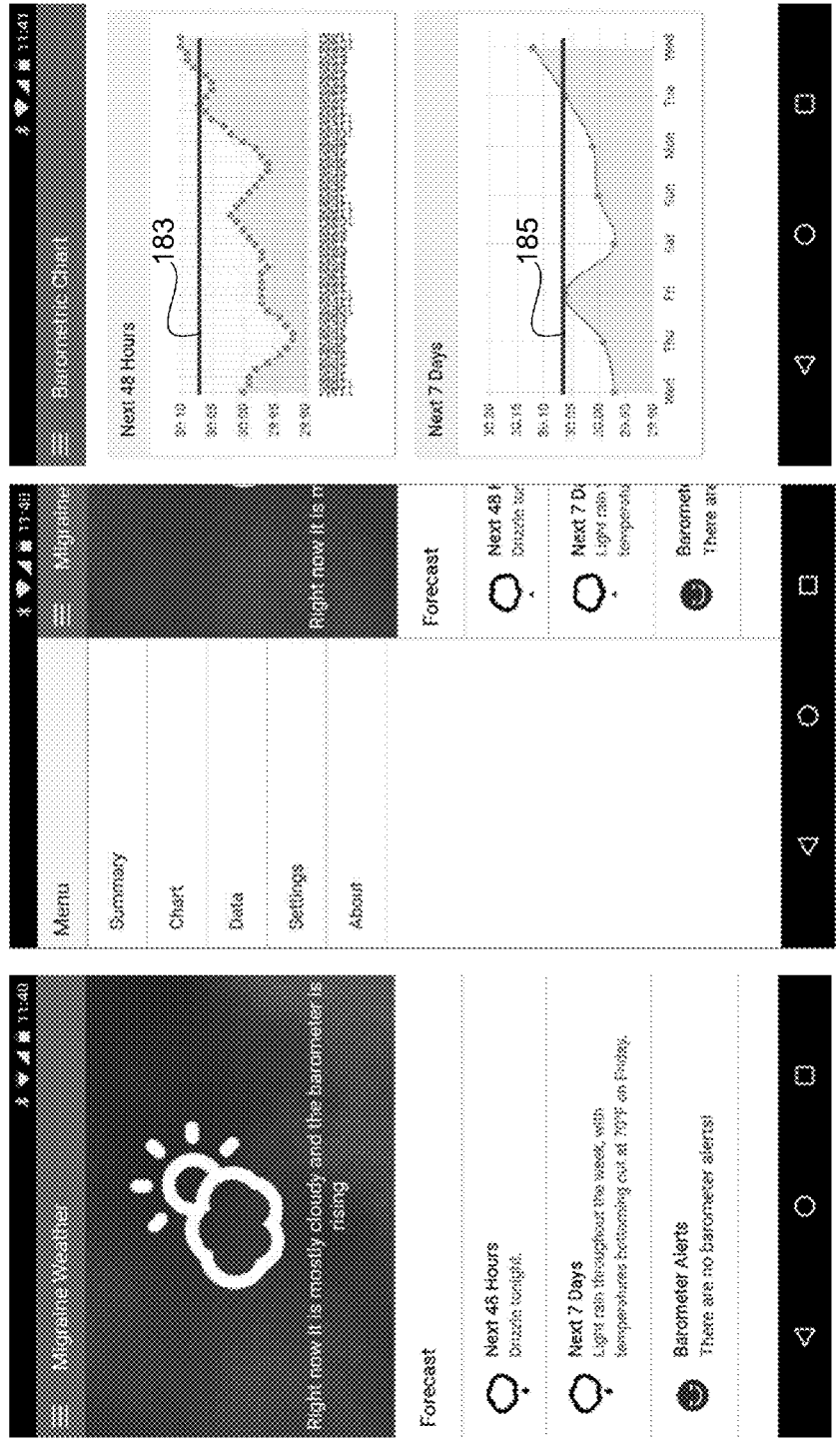
FIG. 4 shows features of an exemplary migraine weather "app" homepage according to aspects of the present invention.
FIG. 5 shows features of a menu of the homepage of FIG. 4.
FIG. 6 shows two charts showing barometric forecasts in terms of hours and days.

Features of an exemplary migraine weather app home page according to an exemplary embodiment of the present invention are shown in FIGS. 4-5. The exemplary forecast information shown in FIG. 4 may alert the user a selected number of days in advance of possible changes in the particular atmospheric condition that causes and/or contributes to the user's involuntary physical distress. For example, the forecast information shown in FIG. 4 indicates that the barometer is rising, but that there currently are no barometer alerts. The forecast may alert the user a selected number of hours in advance of likely changes in the particular atmospheric condition, again barometric pressure, such as the next 48 hours, as also shown by the exemplary forecast information in FIG. 4. The exemplary forecast information shown in FIG. 4 provides an overview of current weather and barometric state (rising/falling) along with selectable forecasts for the next forty-eight hours and the next seven days. The barometer alert may be shown based on user preferences. A menu such as shown in FIG. 5 is available via a button on the top left in FIG. 4 or by dragging from the left side of the display screen.

As shown by the exemplary barometric charts in FIG. 6, the meteorological data in the response signal may be organized for presentation on the user device as a chart of the meteorological data subsisting and forecast at the determined geographic location including at least the particular atmospheric condition organized for presentation over the selected time frame. The chart may include an indication of when to initiate the remedy by a graphical indication of a threshold 183, 185 such that the timing of the remedy is prescribed upon the meteorological data crossing the threshold. For example, the threshold 183 shown in the "Next 48 Hours" chart from FIG. 6 may provide the user with an indication that the user should be prepared to implement or already implement the headache relief earplug 10 according to the present invention for amelioration of a possible barometric pressure and/or migraine headache whenever the barometric pressure is forecasted to meet the threshold 183. In this manner, this aspect of the present invention allows the user to be prepared to take the appropriate remedy, e.g. insertion of the headache relief earplug 10, in response to a change in atmospheric conditions, e.g. change in barometric pressure and/or the barometric pressure meeting a certain point. The threshold 183, 185 shown in FIG. 6 may be configured by the user based on the user's past experiences with the atmospheric conditions and/or may be prescribed based on general knowledge and/or studies regarding the correlation of the atmospheric condition and involuntary physical distress. Alternatively, the threshold 183, 185 may be set at a default position, and then adjusted based on the user's experiences and/or information obtained by the "app" from publically available databases regarding the correlation of the atmospheric condition and involuntary physical distress. In indication, such as a sound or visual notification may be provided to the user in response to the atmospheric condition reaching the currently defined threshold 183, 185, thereby obviating the need for the user to continually monitor the exemplary charts shown in FIG. 6.

Figure 7:
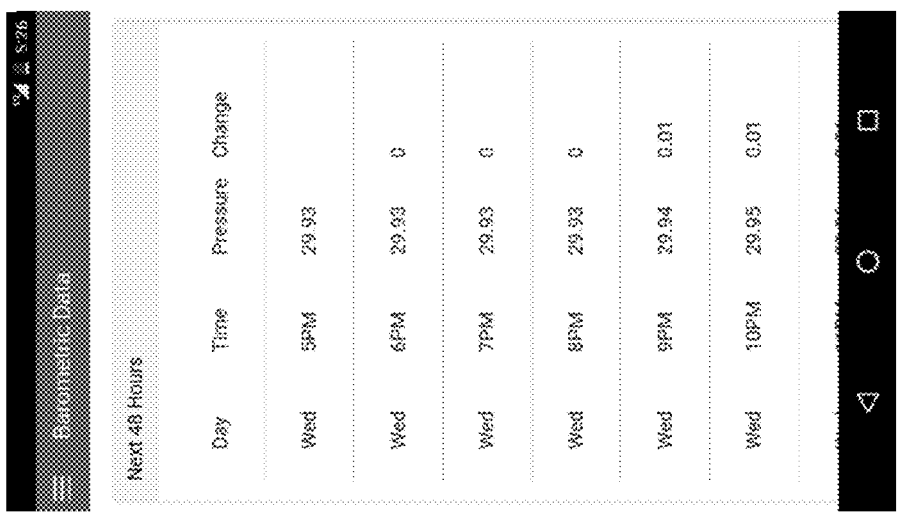
FIG. 7 shows barometric data presented in a tabular format.

As shown in FIG. 7, the meteorological data in the response signal may be formatted for presentation on the user device as tabular data. For instance, if the user chooses "Data" on the menu of FIG. 5, the very detailed barometric data may be presented with pressure drops or rises accurate to 0.01 millibars. As with the charts of FIG. 6, two tables may be made available, one with hour by hour changers over the next forty-eight hours, and another with day by day changes over the next seven days. The exemplary table shown in FIG. 7 can allow the user to be prepared to take the appropriate remedy, e.g. insertion of the headache relief earplug 10, in response to a change in atmospheric conditions, e.g. change in barometric pressure and/or the barometric pressure meeting a certain point.

Figure 8:
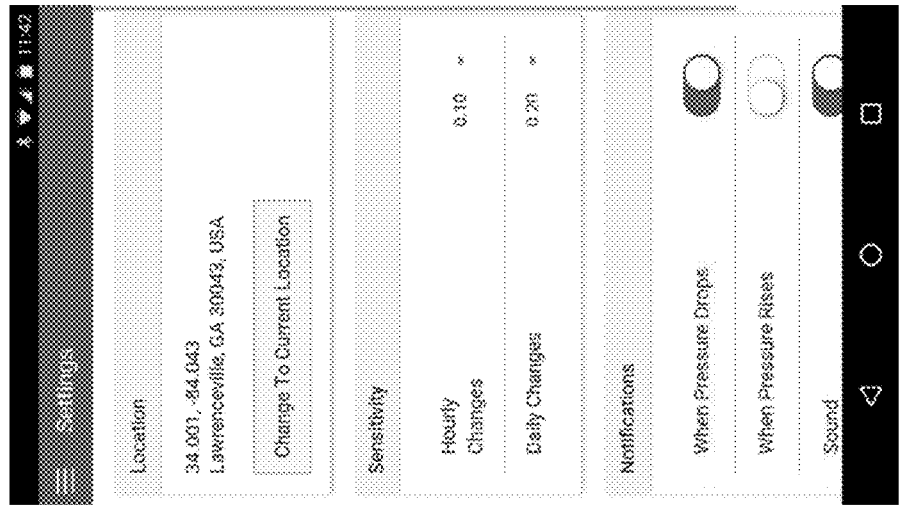
FIG. 8 shows settings made available by the menu of FIG. 5.

As shown in FIG. 8, instead of the "current location" (such as determined by a GPS tracker), the menu settings may be used to select a static location by latitude and longitude. The signal received over the network from the user device at the server may include an indication of a requested granularity of the meteorological data sent in the response signal. Such granularity may for instance be set in the menu settings as shown in FIG. 8 to allow the sensitivity of the data to be selected (e.g. hourly and daily) as well as when (on or off; pressure rise/drop) and how the app should issue notifications (sound or vibration). For instance, once a day the device may be set to check for a drop or rise above 0.20 millibars in a single hour anytime in the next 7 days. If one is found, the user is notified in the morning, but reminded that this is an early warning and weather conditions change often. Twenty-four hours before the event a second notification is shown to the user and the exact time of the pressure drop or rise is shown. As shown in FIG. 8, the "app" may be configured to send the user notifications in accordance with the various exemplary embodiments of the invention so that the user can implement the headache relief earplug 10, or other appropriate remedy, to ameliorate physical distress that may be caused by the atmospheric condition that can cause the physical distress in the user. The notifications can include an indication, whether visual or aural, that informs the user of the impending atmospheric condition so as to allow the user implement the appropriate remedy or an indication that instructs the user to implement the appropriate remedy at a specific time.

Alternatively, the headache relief earplugs 10 may be inserted into the user's ear canal(s) after headache symptoms have begun, and the headache relief earplugs 10 are configured to reduce the duration and severity of the headache symptoms. The headache relief earplugs 10 may be worn in the user's ear canal(s) for any duration of time, and preferably the amount of time required for equilibration of pressure external to the ear canal(s) with pressure internal to the ear canal(s), such as the pressure that exists within one or more sinuses of the user. This amount of time may vary from 3 to 24 hours, but it is understood that the present invention is not limited to any particular amount of time regarding the duration the earplugs are left within the user's ear canal(s). In the event that the user has inserted the headache relief earplugs 10 within the ear canal(s) prior to the onset of headache symptoms, and no headache symptoms are experience, the user may then leave the headache relief earplugs 10 within the ear canal(s) until the conditions which were likely to have caused headache symptoms have passed. The headache relief earplugs 10 should preferably be inserted into the user's ear canal(s) a sufficient depth so as to allow at least one the plurality of ribs 17 to form an airtight seal with the ear canal(s). In this manner, the exchange of air occurs through the pressure regulator 14 so that the leak rate of the pressure regulator 14 adjusts for changes in pressure that may result in the onset or worsening of headache symptoms.

The above described platform can be used to help Neurology offices and headache clinics. For instance, the "app" according to the present invention may be configured to notify doctors and/or their patients before a barometric event occurs. The doctors or doctors' offices may sign up with the "app" according to the present invention, and the platform places a form on their website for their patients to join a mailing list. Weather can then be monitored for the area surrounding the doctor's office. When a barometric event is about to occur their patients will receive an email letting them know and reminding them to follow their doctors advice. The platform works with the doctors to help them write the email. At the same time, the scheduling staff will get an alert letting them know to prepare for extra walk in appointments. This will be particularly useful to headache clinics that treat severe migraine attacks with IV infusions or NSAID injections. The "app" according to the present invention can help them know in advance when an increase in demand for these treatments may occur, and even when to suggest that certain patients come in for these treatments before the pain begins. This results in decreased pain for patients and increased revenue for doctors.

It will thus be seen that the objects set forth above, among those made apparent from the preceding description, are efficiently attained and, since certain changes may be made in the above article without departing from the scope of this invention, it is intended that all matter contained in this disclosure or shown in the accompanying drawings, shall be interpreted, as illustrative and not in a limiting sense. It is to be understood that all of the present figures, and the accompanying narrative discussions of corresponding embodiments, do not purport to be completely rigorous treatments of the invention under consideration. It is to be understood that the above-described arrangements are only illustrative of the application of the principles of the present invention. Numerous modifications and alternative arrangements may be devised by those skilled in the art without departing from the scope of the present invention.

What is claimed is:

1. A method, comprising:

receiving a signal over a network connection from a device of a user requesting meteorological data pertaining to a particular atmospheric condition, the user requesting the meteorological data to assist the user in timing of a remedy to ameliorate involuntary physical distress in the user caused by a change in the particular atmospheric condition, determining a current geographic location or an associated geographic location of the user device, retrieving meteorological data subsisting and forecast at the determined geographic location, and sending a response signal over the network connection to the user device, the response signal having the meteorological data subsisting and forecast at the determined geographic location including at least the particular atmospheric condition organized for presentation over a selected time frame so that the timing of the remedy is ascertainable in case the atmospheric condition is forecast to change in such a way as to cause the involuntary physical distress in the user;

wherein the particular atmospheric condition is barometric pressure; and wherein the change in the barometric pressure is an increase in the barometric pressure, a decrease in the barometric or the barometric pressure meeting a certain predefined threshold level: and wherein the remedy to ameliorate the involuntary physical distress caused by the change in the barometric pressure comprises at least one earplug having a body having a first end, a second end and a longitudinal axis extending from the first end to the second end, a bore defined within the body and extending from the first end to the second end along the longitudinal axis of the body, and a pressure regulator positioned within the bore and providing an air flow rate of $3.4 \times 10^{-6}$ to $7.8 \times 10^{-5}$ cc/sec through the bore.

2. The method of claim 1, wherein the pressure regulator of the earplug is comprised of a porous material having a porosity of 1.3 to 2 microns.

3. The method of claim 1, wherein the meteorological data in the response signal is organized for presentation on the user device as a chart of the meteorological data subsisting and forecast at the determined geographic location including at least the barometric pressure organized for presentation over the selected time frame.

4. The method of claim 3, wherein the chart indicates when to initiate the remedy by a graphical indication of a threshold such that the timing of the remedy is prescribed upon the meteorological data crossing the threshold.

5. The method of claim 1, wherein the forecast alerts the user a selected number of hours in advance of likely changes in the barometric pressure.

6. The method of claim 1, wherein the response signal received over the network connection to the user device includes an indication of when to initiate insertion of the at least one earplug into the user's ear canals.

7. Apparatus, comprising:
at least one processor; and
at least one storage device including a computer program, the at least one storage device and the computer program configured to, with the at least one processor, cause the apparatus to carry out the method of claim 1.

8. A method, comprising:
sending a request signal over a network connection from a device of a user requesting meteorological data pertaining to a particular atmospheric condition, the user requesting the meteorological data to assist the user in timing of a remedy to ameliorate involuntary physical distress in the user caused by a change in the particular atmospheric condition, the request signal including a current geographic location or an associated geographic location of the user device, and
receiving a response signal over the network connection to the user device, the response signal having the requested meteorological data subsisting and forecast at the geographic location including at least the particular atmospheric condition organized for presentation over a selected time frame so that the timing of the remedy is ascertainable in case the atmospheric condition is forecast to change in such a way as to cause the involuntary physical distress in the user;
wherein the particular atmospheric condition is barometric pressure; and
wherein the remedy to ameliorate the involuntary physical distress caused by the change in the barometric pressure comprises at least one earplug having a body having a first end, a second end and a longitudinal axis extending from the first end to the second end, a bore defined within the body and extending from the first end to the second end along the longitudinal axis of the body, and a pressure regulator positioned within the bore and providing an air flow rate of $3.4 \times 10^{-6}$ to $7.8 \times 10^{-5}$ cc/sec through the bore.

9. A nontransitory computer readable medium having a computer program stored thereon that is executable by a processor for causing a portable electronic display device to carry out the method of claim 8.

10. An apparatus comprising at least one processor and at least one memory including an application that is executable by the at least one processor to cause the apparatus at least to carry out the method of claim 8.

11. The method of claim 8, wherein the pressure regulator of the earplug is comprised of a porous material having a porosity of 1.3 to 2 microns.

12. The method of claim 8, wherein the meteorological data in the response signal is organized for presentation on the user device as a chart of the meteorological data subsisting and forecast at the determined geographic location including at least the barometric pressure organized for presentation over the selected time frame.

13. The method of claim 12, wherein the chart indicates when to initiate the remedy by a graphical indication of a threshold such that the timing of the remedy is prescribed upon the meteorological data crossing the threshold.

14. The method of claim 8, wherein the response signal received over the network connection to the user device includes an indication of when to initiate insertion of the at least one earplug into the user's ear canals.

15. A method, comprising:
receiving a signal over a network connection from a device of a user requesting meteorological data pertaining to a particular atmospheric condition, the user requesting the meteorological data to assist the user in timing of a remedy to ameliorate involuntary physical distress in the user caused by a change in the particular atmospheric condition,
determining a current geographic location or an associated geographic location of the user device,
retrieving meteorological data subsisting and forecast at the determined geographic location, and
sending a response signal over the network connection to the user device, the response signal having the meteorological data subsisting and forecast at the determined geographic location including at least the particular atmospheric condition organized for presentation over a selected time frame so that the timing of the remedy is ascertainable in case the atmospheric condition is forecast to change in such a way as to cause the involuntary physical distress in the user;
wherein the particular atmospheric condition is barometric pressure; and
wherein the remedy to ameliorate the involuntary physical distress caused by the change in the barometric pressure comprises at least one earplug having a body having a first end, a second end and a longitudinal axis extending from the first end to the second end, a bore defined within the body and extending from the first end to the second end along the longitudinal axis of the body, and a pressure regulator positioned within the bore and providing an air flow rate of $3.4 \times 10^{-6}$ to $7.8 \times 10^{-5}$ cc/sec through the bore.

16. The method of claim 15, wherein the pressure regulator of the earplug is comprised of a porous material having a porosity of 1.3 to 2 microns.

17. The method of claim 15, wherein the response signal received over the network connection to the user device includes an indication of when to initiate insertion of the at least one earplug into the user's ear canals.

18. The method of claim 15, wherein the meteorological data in the response signal is organized for presentation on the user device as a chart of the meteorological data subsisting and forecast at the determined geographic location including at least the barometric pressure organized for presentation over the selected time frame.

19. The method of claim 18, wherein the chart indicates when to initiate the remedy by a graphical indication of a threshold such that the timing of the remedy is prescribed upon the meteorological data crossing the threshold.

20. The method of claim 15, wherein the forecast alerts the user a selected number of hours in advance of likely changes in the barometric pressure.

21. Apparatus, comprising:
at least one processor; and
at least one storage device including a computer program, the at least one storage device and the computer program configured to, with the at least one processor, cause the apparatus to carry out the method of claim 15.

22. A method, comprising:
receiving a signal over a network connection from a device of a user requesting meteorological data pertaining to a particular atmospheric condition, the user requesting the meteorological data to assist the user in timing of a remedy to ameliorate involuntary physical distress in the user caused by a change in the particular atmospheric condition,
determining a current geographic location or an associated geographic location of the user device,
retrieving meteorological data subsisting and forecast at the determined geographic location, and
sending a response signal over the network connection to the user device, the response signal having the meteorological data subsisting and forecast at the determined geographic location including at least the particular atmospheric condition organized for presentation over a selected time frame so that the timing of the remedy is ascertainable in case the atmospheric condition is forecast to change in such a way as to cause the involuntary physical distress in the user;
wherein the particular atmospheric condition is barometric pressure;
wherein the remedy to ameliorate the involuntary physical distress caused by the change in the barometric pressure comprises at least one earplug having a body having a first end, a second end and a longitudinal axis extending from the first end to the second end, a bore defined within the body and extending from the first end to the second end along the longitudinal axis of the body, and a pressure regulator comprised of a porous material having a porosity of 1.3 to 2 microns positioned within the bore; and
wherein the pressure regulator of the earplug is configured to provide an air flow rate of $3.4\times10^{-6}$ to $7.8\times10^{-5}$ cc/sec through the bore.

23. The method of claim 22, wherein the response signal received over the network connection to the user device includes an indication of when to initiate insertion of the at least one earplug into the user's ear canals.

24. The method of claim 22, wherein the meteorological data in the response signal is organized for presentation on the user device as a chart of the meteorological data subsisting and forecast at the determined geographic location including at least the barometric pressure organized for presentation over the selected time frame.

25. The method of claim 24, wherein the chart indicates when to initiate the remedy by a graphical indication of a threshold such that the timing of the remedy is prescribed upon the meteorological data crossing the threshold.

26. The method of claim 22, wherein the forecast alerts the user a selected number of hours in advance of likely changes in the barometric pressure.

27. Apparatus, comprising:
at least one processor; and
at least one storage device including a computer program, the at least one storage device and the computer program configured to, with the at least one processor, cause the apparatus to carry out the method of claim 22.

28. A method, comprising:
sending a request signal over a network connection from a device of a user requesting meteorological data pertaining to a particular atmospheric condition, the user requesting the meteorological data to assist the user in timing of a remedy to ameliorate involuntary physical distress in the user caused by a change in the particular atmospheric condition, the request signal including a current geographic location or an associated geographic location of the user device, and
receiving a response signal over the network connection to the user device, the response signal having the requested meteorological data subsisting and forecast at the geographic location including at least the particular atmospheric condition organized for presentation over a selected time frame so that the timing of the remedy is ascertainable in case the atmospheric condition is forecast to change in such a way as to cause the involuntary physical distress in the user;
wherein the particular atmospheric condition is barometric pressure;
wherein the change in the barometric pressure is an increase in the barometric pressure, a decrease in the barometric or the barometric pressure meeting a certain predefined threshold level; and
wherein the remedy to ameliorate the involuntary physical distress caused by the change in the barometric pressure comprises at least one earplug having a body having a first end, a second end and a longitudinal axis extending from the first end to the second end, a bore defined within the body and extending from the first end to the second end along the longitudinal axis of the body, and a pressure regulator positioned within the bore and providing an air flow rate of $3.4\times10^{-6}$ to $7.8\times10^{-5}$ cc/sec through the bore.

29. A nontransitory computer readable medium having a computer program stored thereon that is executable by a processor for causing a portable electronic display device to carry out the method of claim 28.

30. An apparatus comprising at least one processor and at least one memory including an application that is executable by the at least one processor to cause the apparatus at least to carry out the method of claim 28.

31. The method of claim 28, wherein the pressure regulator is comprised of a porous material having a porosity of 1.3 to 2microns positioned within the bore.

32. The method of claim 28, wherein the meteorological data in the response signal is organized for presentation on the user device as a chart of the meteorological data subsisting and forecast at the determined geographic location including at least the barometric pressure organized for presentation over the selected time frame.

33. The method of claim 32, wherein the chart indicates when to initiate the remedy by a graphical indication of a threshold such that the timing of the remedy is prescribed upon the meteorological data crossing the threshold.

34. The method of claim 28, wherein the response signal received over the network connection to the user device includes an indication of when to initiate insertion of the at least one earplug into the user's ear canals.

* * * * *